United States Patent [19]
Desantis

[11] Patent Number: 6,037,494
[45] Date of Patent: Mar. 14, 2000

[54] PROCESS FOR THE CRYSTALLIZATION FROM A LINEAR OR BRANCHED (C5-C6) ALCOHOL OR THEIR MIXTURES OF (S)-N,N'-BIS[2-HYDROXY-1-(HYDROXYMETHYL)ETHYL]-5-[(2-HYDROXY-1-OXOPROPYYL)AMINO]-2,4,6-TRIIODO-1,3-BENZENDICARBOXAMIDE

[75] Inventor: Nicola Desantis, Cernusco Sul Naviglio, Italy

[73] Assignee: Bracco International B.V., Netherlands

[21] Appl. No.: 09/020,424

[22] Filed: Feb. 9, 1998

[30] Foreign Application Priority Data

Feb. 11, 1997 [IT] Italy ............... PCT/IB97/00106

[51] Int. Cl.⁷ ................................. C07C 231/22
[52] U.S. Cl. ............. 564/153; 424/9.452; 424/9.454; 564/152
[58] Field of Search ................. 564/153, 152; 424/9.452, 9.454

[56] References Cited

U.S. PATENT DOCUMENTS 5,571,941  11/1996  Villa et al. .................. 564/153
5,698,739  12/1997  Sovak ......................... 564/153

*Primary Examiner*—Shailendra Kumar
*Attorney, Agent, or Firm*—Nixon & Vanderhye

[57] ABSTRACT

Disclosed is a new process for the crystallization of (S)-N,N'-bis[2-hydroxy-1-(hydroxymethyl)ethyl]-5-[(2-hydroxy-1-oxopropyl)amino]-2,4,6-triiodo-1,3-benzendicarboxamide (I), using a linear or branched (C5–C6) alcohol or their mixtures.

12 Claims, No Drawings

PROCESS FOR THE CRYSTALLIZATION FROM A LINEAR OR BRANCHED (C5-C6) ALCOHOL OR THEIR MIXTURES OF (S)-N, N'-BIS[2-HYDROXY-1-(HYDROXYMETHYL) ETHYL]-5-[(2-HYDROXY-1-OXOPROPYYL) AMINO]-2,4,6-TRIIODO-1,3-BENZENDICARBOXAMIDE

TECHNICAL FIELD

This invention refers to a new process for the crystallization of (S)-N,N'-bis[2-hydroxy-1-(hydroxymethyl)ethyl]-5-[(2-hydroxy-1-oxopropyl)amino]-2,4,6-triiodo-1,3-benzendicarboxamide (I), using a linear or branched (C5–C6) alcohol or their mixtures.

BACKGROUND ART

The compound (I) is best known as Iopamidol, which is one of the world top compounds in the field of non-ionic X-ray contrast media.

The syntheses of Iopamidol known in literature, for instance the one described in GB 1472050, foresee a final purification at the end of the process, by using ion-exchange resins and successive recrystallization from EtOH or iso-PrOH.

Recently the patent application WO-A-95/04031 mentions different solvents (n-BuOH, sec-BuOH, iso-BuOH and/or t-BuOH) from which Iopamidol crystallizes. Butyl alcohols, especially 2-butanol, are used in a manner similar to that mentioned above for ethanol. It is claimed that butyl alcohols are more easily removed than ethanol from the final product in the drying step.

A more recent application EP-A-0 747 344 discloses the use of propanol or isopropanol as crystallization solvent to overcome the problem of the formation of pasty products during the crystallization.

Another recent application IT95A001429 discloses the use of monoether of the ethylenglycol (e.g. Cellosolve® or Metilcellosolve®) as crystallization solvent for Iopamidol. This procedure allows the crystallization of Iopamidol starting from a product with a purity grade comprised between 99–99.5%.

DETAILED DESCRIPTION OF THE INVENTION

We have now surprisingly found out that, and this is part of this invention, Iopamidol can be easily crystallized from the homologous (C5–C6) alcoholic solvents, with industrially acceptable yields and giving a product which meets the pharmacopoeia standards.

These solvents are very uncommon as crystallization solvent for their characteristics of high boiling point and low water solubility, especially for compound like Iopamidol very soluble in water. Therefore, the skilled technician would not have found a suggestion in the prior-art for using these alcohols.

The preferred solvents are selected from the following groups: hexanol, pentanol, 2-pentanol and 3-pentanol mixture, and iso-pentanol.

The improvement of this invention consists in the use of solvents able to give azeotropes with water forming two separate layers; the lower level has a minimal removable solvent content, while the upper one can be recycled.

This improvement is remarkable from the industrial point of view because it reduces the amount of solvent used and at the same time gives a product in accordance with pharmacopoeia standards, which have changed over the years (see the European Pharmacopoeia III ed. 1997 or USP XXIII-NF, 1996, V° suppl.) reducing the related substances content from 0.5% to 0.25%.

The achieved improvement, compared to the already used solvents cited in the above patents, is connected with the water percentage of the azeotropic mixture and the ability of the azeotrope to give two separate layers.

Despite WO-A-95/04031 describes the possibility to have the azeotropic mixture obtained by distillation separated in its components, that its true only for n-BuOH and iso-BuOH and not for all the claimed C4 alcohols, as cited in the following data regarding the azeotropes with water from "HANDBOOK OF CHEMISTRY AND PHYSICS", 68th Ed.

When the data are missing, experimental data are reported, obtained with the following procedure: 50 g of the solvent and 50 g of water are mixed in a reactor, equipped with stirrer, a Markusson settler. Then the mixture is refluxed, the azeotropic layers are collected and the water content is determined by Karl-Fisher method.

| SOLVENT | % WATER AZEOTROPE | IN % WATER LAYER | UPPER % WATER LAYER | LOWER AZEOTROPE TYPE |
| --- | --- | --- | --- | --- |
| Ethanol | 4.4% | | | homogeneous |
| 1-Propanol | 28.2% | | | homogeneous |
| iso-Propanol | 12.2% | | | homogeneous |
| 1-Butanol | 44.5% | 20.1% | 92.3% | heterogeneous |
| 2-Butanol | 32% | | | homogeneous |
| iso-Butanol | 30% | 15.0% | 91.3% | heterogeneous |
| tert-Butanol | 11.75% | | | homogeneous |
| 1-Pentanol | 55% | 12.4% (exp.) | 95.05% (exp.) | heterogeneous |
| 2-Pentanol | 36.5% | 12.8% (exp.) | 86.2% (exp.) | heterogeneous |
| iso-Pentanol | 49.6% | 12.7% (exp.) | 81.2% (exp.) | heterogeneous |
| 3-Pentanol | 35% | 9.9% | 94.5% | heterogeneous |
| n-Hexanol | 67.2% | 7.2% | 99.42% | heterogeneous |

It is easy to realize that the solvents of this invention, are those with a higher water percentage in the upper layer and form separate layers, except for n-BuOH and iso-BuOH.

According to the process of this present invention, the recycled upper layer has a very low residual water content with respect to that of n-BuOH and iso-BuOH.

Furthermore, the residual water content present in the upper layer of the solvents of this invention is lower than 15% (w/w) and so that Iopamidol can be crystallized, if necessary, without anidrifying them. Thus according to this invention the recycling of the organic layer becomes more advantageous from the industrial point of view since the costs for the solvents are curbed and the crystallization time are reduced.

Furthermore, as described in the Examples, the upper layer can be cooled and used it for washing the wet filtration cake. This procedure is absolutely new and is a great improvement from the industrial point of view.

The recovery of the solvent is easy and the upper layer can be directly used in the process of this invention without anidrifying it. In this way the industrial process for the recovery of the solvent does not need elaborate systems or processes such as pervaporation or the simple addition of a little amount of a third solvent to the binary azeotropic mixture, for example toluene or cyclohexane, able to form a ternary azeotrope with water.

If the (C2–C4) alcohols are used, it is necessary to anidrify the recovered solvent using, for example, one of the above cited procedures.

In the process of this invention a crude aqueous solution of Iopamidol 5–25% (w/w) is concentrated under vacuum at a pressure of 3–12 mmHg or atmospheric pressure, at a temperature comprised between 50 and 100° C. to have a water residual content comprised between 15–35% (w/w). Then the mixture is heated or cooled, depending on the case, and the crystallization solvent is added at a temperature comprised between 85–95° C., maintaining this temperature during the addition.

The amount of the solvent to be used is from 0.8 to 6 times (w/w) with respect to the amount of theoretical Iopamidol. Preferably, the solvent amount is from 0.8 to 4.5 times (w/w) with respect to the amount of theoretical Iopamidol. The water content is not considered, because water-saturated solvents can be used.

Then the mixture is azeotropic distilled, recycling the upper layer until the two layers are dissolved. Sometimes the distillation can be carried out to have a water residual content from 4 to 10% in the floating liquid. The solid can precipitate during this step, eventually by germination. In some cases it is possible to add the solvent in two or three consecutive portions.

In some cases, depending from the solvent, when the solid is beginning to crystallize in the lower layer, the distillation can be stopped and the mixture is cooled at the temperature from 60 to 80° C. and then germinate.

After the precipitation of the solid, the distillation can be resumed until the water final content in the floating liquid is reached.

Then the temperature is taken to 17–25° C. and maintained for 1–5 hours. Then the solid is filtered, washed with dry solvents or with a quantity of the wet recycled solvent from the upper layer of the distilled azeotropic mixture.

The amount of the solvent is from 0.4 to 2 times (w/w) with respect to the amount of theoretical Iopamidol, preferably from 0.4 to 1 time.

The wet product is dried under a pressure comprised between 1–10 mmHg, preferably between 3–7 mmHg at a temperature comprised between 75° C. and 95° C. during at least 16 hours.

This procedure has no effect on the quality of the product and in this way the residual solvents are removed easily. The product is very stable, and decomposes at about 300° C. without melting (see for example Merck Index 12th edition).

After drying, no smell is detectable and surprisingly the residual content of the crystallization solvent is lower than 60 ppm.

The following table illustrates the content of the residual crystallization solvent in the final product and in the cited references, compared with the Examples of the present invention. In particular, the data regarding the ethanol as crystallization solvent are obtained using the procedure of the cited patent.

| SOLVENT | RESIDUAL CONTENT | REFERENCES |
| --- | --- | --- |
| Ethanol | 490 ppm | GB 1472050 |
| Ethanol | 270 ppm | GB 1472050 |
| Ethanol | 370 ppm | GB 1472050 |
| Sec-butanol | 200 ppm | WO-A-9504031 (EX. 1) |
| Sec-butanol | 180 ppm | WO-A-9504031 (EX: 2) |
| Sec-butanol | 100 ppm | WO-A-9504031 (EX. 3) |
| n-butanol | 70 ppm | WO-A-9504031 (EX. 4) |
| n-butanol | 80 ppm | WO-A-9504031 (EX. 5) |
| sec-butanol | 100 ppm | WO-A-9504031 (EX. 6) |
| t-butanol | 150 ppm | WO-A-9504031 (EX. 7) |
| n-pentanol | 40 ppm | Example 1 |
| iso-pentanol | 30 ppm | Example 2 |
| 2-pentanol/3-pentanol | 25 ppm | Example 3 |
| n-hexanol | 25 ppm | Example 4 |
| n-hexanol | 35 ppm | Example 5 |

Two preparations on industrial scale are reported in the Experimental part to demonstrate the improvement of the process of this invention. All the reported examples give a product with a residual content of organic by-products lower than 0.25%, according to the more recent Pharmacopoeias.

The following examples serve to illustrate this invention and are not, in any way, to be considered as a limitation thereof. The water content in the azeotrope and in the final product was determined by the Karl-Fisher method, while the content of the solvent in the final product was determined by gas-chromatography.

EXAMPLE 1

1000 g of a 50% (w/w) crude aqueous solution of Iopamidol containing 0.4% of organic by-products is concentrated at atmospheric pressure at 100° C. to obtain a water content comprised between 22% and 26% (w/w).

After cooling to about 95° C., 600 g of n-pentanol are added during an hour without cooling the solution. Then the solution is refluxed recycling the upper layer of the azeotrope mixture. The product precipitates during this step.

Then the mixture is distilled to have a 7–8% residue content of water in the floating liquid. Then the mixture is refluxed for 60 min. then cooled to 25° C. and kept at this temperature for two hours. The product is filtered, washed with n-pentanol and dried at 80° C., 12 mmHg for 12 hours.

Yield: 94%; Residual solvent:40 ppm

EXAMPLE 2

800 kg of a 70% (w/w) crude aqueous solution of Iopamidol containing 0.3% of organic by-products is concentrated at 12 mmHg pressure and 50° C. to obtain a water content comprised between 25% and 30% (w/w) determined by Karl Fisher titration. Then the mixture is concentrated at atmospheric pressure at 100° C. to obtain a residual water content comprised between 20% and 25% (w/w). 400 kg of iso-pentanol are added to the solution in 2 hours and very slowly in the first 15 min. The azeotrope is distilled using a distilling apparatus equipped with a settler recycling the upper phase. The distillation is continued to have a 10% (w/w) residual content of water determined by Karl Fisher titration. During this step the product precipitates spontaneously under crystalline form, without germination. Then 200 kg of dry iso-pentanol are added, maintaining the azeotropic distillation, to reach a 4–5% (w/w) of the residual content of water in the floating liquid. The mixture is refluxed for 1 hour, cooled in 3 hours to 15–20° C. and finally filtered on centrifuge, washed with two portions of 100 kg of the recycled solvent from the upper phase of the azeotrope. Then the product is dried at 3 mmHg for 8 hours at 60° C. and for other 8 hours at 75° C.

Yield: 95%; Residual solvent: 30 ppm

EXAMPLE 3

10000 g of a 50% (w/w) crude aqueous solution of Iopamidol containing 0.4% of organic by-products is concentrated at atmospheric pressure at 100° C. to obtain a water content comprised between 22% and 26% (w/w). After cooling to about 95° C., 4000 g of a mixture of 30% of 2-pentanol and 70% of 3-pentanol in 3 hours is added without cooling the solution to 92° C. Then the solution is refluxed recycling the upper layer of the azeotrope mixture. The product precipitates during this step. Then the mixture is distilled to have a 5% residue content of water in the floating liquid. Then the mixture is refluxed for 60 min., then cooled to 25° C. and kept at this temperature for 3 hours. The product is filtered, washed with 2000 g of the upper phase of the azeotrope mixture. Then the product is dried at 80° C. with pressure of 12 mmHg during 12 hours.

Yield: 93%; Residual solvent: 25 ppm

EXAMPLE 4

100 g of a 70% (w/w) crude aqueous solution of Iopamidol containing 0.3% of organic by-products is concentrated at atmospheric pressure at 100° C. to obtain a water content comprised between 22% and 35% (w/w). After cooling to about 95° C., 300 g of a n-hexanol saturated with water are added during about 1 hour without cooling the solution. Then the solution is refluxed recycling the upper layer of the azeotrope mixture. The product precipitates during this step. Then the mixture is distilled to have a 7.2% residual water content in the floating liquid. Then the mixture is refluxed for 60 min., then cooled to 25° C. and kept at this temperature for 2 hours. The product is filtered, washed with 50 g of the upper phase of the azeotrope. Then the product is dried at 80° C. with pressure of 12 mmHg during 12 hours.

Yield: 90%; Residual solvent: 25 ppm

EXAMPLE 5

200 kg of a 70% (w/w) crude aqueous solution of Iopamidol containing 0.3% of organic by-products is concentrated at atmospheric pressure at 100° C. to obtain a water content comprised between 22% and 35% (w/w). After cooling to about 95° C., 100 kg of a n-hexanol saturated with water are added during about 1 hour, without cooling the solution. Then the solution is refluxed recycling the upper layer of the azeotrope mixture to obtain the two layers system, where Iopamidol is beginning to crystallize in the lower layer. Then the mixture is cooled to a temperature comprised between 50–80° C. and some germs are added to the mixture. Then the mixture is stirred at this temperature until the product terminates its crystallization (about 1 hour). Then the mixture is refluxed again recycling the upper layer of the azeotrope mixture distilled, to reach a 7.2% residual content of water in the floating liquid. The mixture is refluxed for 60 min., then cooled to 25° C. and kept at this temperature for 3 hours. The product is filtered, washed with two portions of 50 kg of the upper phase of azeotrope.

The product is dried at 95° C. with pressure of 3 mmHg during 20 hours.

Yield: 93%; Residual solvent: 35 ppm

EXAMPLE 6

200 kg of the mother liquors from the crystallization described in the Example 5, containing 7% of water, are distilled in a 300 L batch distillator, equipped with an impeller, a heating system using steam, to give a residue of about 50 kg. 130 kg of the upper layer with 7% of water and less than 1% of by-products (determined by GC) are recovered in the condenser and recycled.

I claim:
1. A process for purifying L-5-α-hydroxypropionylamino-2,4,6-triiodo-isophthalic acid bis-(1,3-dihydroxyisopropylamide)(Iopamidol) comprising the steps of:

dissolving a crude solid of Iopamidol in a linear or branched C5–C6 alcohol or their mixtures, and crystallizing pure Iopamidol therefrom.

2. A process according to claim 1, in which the crystallization solvent is selected in the group consisting of: hexanol, pentanol, 2-pentanol and 3-pentanol mixture, iso-pentanol.

3. A process according to claim 1, in which the crystallization solvent is hexanol.

4. A process according to claim 1, in which the crystallization solvent is pentanol.

5. A process according to claim 1, in which the crystallization solvent is 2-pentanol and 3-pentanol mixture.

6. A process according to claim 1, in which the crystallization solvent is iso-pentanol.

7. A process, according to claim 1, for the crystallization of Iopamidol to give said compound in a crystalline form and in accordance to the pharmacopeia standards comprising the following steps:

a) concentration under atmospheric or reduced pressure of an aqueous solution of Iopamidol 5–25% (w/w) at a temperature comprised between 50–100° C., to reach a residual water content comprised between 15–35%;

b) addition of the crystallization solvent at 85–95° C., maintaining this temperature during the addition;

c) distillation of the azeotropic mixture, recycling the upper layer until the two layers are dissolved; or termination of the distillation when the solid begins to crystallize in the mixture, cooling of the mixture at a temperature comprised between 60–80° C., and then germination;

d) the distillation can be resumed to reach a final water residual content comprised between 4–10% in the floating liquid;

e) the temperature is then taken to 17–25° C. and kept for 1–5 hours;

f) filtration of the resulting precipitate, washed with the solvent;

g) under-vacuum drying of the solid under reduced pressure at a temperature comprised between 75–95° C., during at least 16 hours.

8. A process according to claim 7, in which the crystallization solvent is added in amounts from 0.8 to 6 times with respect to the amount of theoretical Iopamidol.

9. A process according to claim 7, in which the crystallization solvent is added in amounts from 0.8 to 4.5 times with respect to the amount of theoretical Iopamidol.

10. A process according to claim 7, in which the solvent for washing the filtrate is the wet recycled solvent from the upper layer of the azeotropic mixture cooled to room temperature.

11. A process according to claim 10, in which the solvent for washing the filtrate is added in amounts from 0.4 to 2 times with respect to the amount of theoretical Iopamidol.

12. A process according to claim 10, in which the solvent for washing the filtrate is added in amounts from 0.4 to 1 times with respect to the amount of theoretical Iopamidol.

* * * * *